United States Patent [19]
Woodhead et al.

[11] Patent Number: 5,148,125
[45] Date of Patent: Sep. 15, 1992

[54] DIELECTRIC CONSTANT MONITOR

[75] Inventors: Ian M. Woodhead; Stephen J. J. Hirsch, both of Christchurch, New Zealand

[73] Assignee: Lincoln College, Christchurch, New Zealand

[21] Appl. No.: 721,921

[22] Filed: Jun. 21, 1991

[30] Foreign Application Priority Data

Mar. 3, 1989 [NZ] New Zealand .............................. 228210

Related U.S. Application Data

[62] Division of Ser. No. 485,747, Mar. 1, 1990, abandoned.

[51] Int. Cl.$^5$ ............................................. G01R 27/00
[52] U.S. Cl. .................................. 331/135; 331/136; 331/65; 324/682; 324/690
[58] Field of Search .................. 331/135, 136, 65; 324/633, 634, 682, 690

[56] References Cited

U.S. PATENT DOCUMENTS

| | | | |
|---|---|---|---|
| 3,766,496 | 10/1973 | Whitehouse | 331/135 X |
| 3,965,416 | 6/1976 | Friedman | 324/633 |
| 4,291,283 | 9/1981 | Castera | 331/135 X |
| 4,799,028 | 1/1989 | Weaver et al. | 331/135 X |

*Primary Examiner*—Robert J. Pascal
*Attorney, Agent, or Firm*—Nixon & Vanderhye

[57] ABSTRACT

Monitoring of the average dielectric constant in an extended volume of a medium such as soil is achieved using an oscillator incorporating a transmission line to be embedded in the medium. The transmission line is connected as the feedback loop of an amplifier, for one-way propagation of an electrical signal with a delay determined largely by the dielectric properties of the medium, such as its moisture content. The oscillation frequency is indicative of the dielectric constant of the medium.

9 Claims, 3 Drawing Sheets

DIELECTRIC CONSTANT MONITOR

This is a division of application Ser. No. 07/485,747, filed Mar. 1, 1990, now abandoned.

FIELD OF THE INVENTION

This invention relates to electrical oscillators for measuring dielectric properties of materials, in particular but not solely for measurement of soil moisture content. The oscillator frequency depends on the propagation time of a transmission line surrounded by the material to be investigated.

DESCRIPTION OF THE PRIOR ART

Accurate measurement of soil moisture has always been an important requirement in both agriculture and horticulture, usually on a routine basis and throughout each growing season. Other applications also require remote monitoring as a desirable alternative to regular removal of physical samples, such as determination of moisture beneath roadways, embankments and back fill, and in industrial processes. Most techniques currently available however provide only localized measurements whereas under practical conditions moisture is a spatially variable material parameter. Localized measurement devices include tensiometers, and resistance, capacitance or neutron probes, and gravimetric means.

In agricultural applications, repeated measurements would ideally be made at various depths, covering a wide surface area of crop land, and this necessarily involves considerable complexity and cost. It is also usually desirable to determine the moisture content of a large volume of soil relatively quickly and regularly, or even continuously, for instance in order to optimize irrigation as part of an overall crop management program.

Capacitance measurements of dielectric properties are common. The capacitance of a conductor geometry is generally proportional to the dielectric constant K of the surrounding material. K varies with the frequency of the imposed electric field. Frequencies between about 30 MHz and 2 GHz have been chosen for soil moisture measurements in the past, to ensure reasonable independence of the measurements from the various soil types. The dielectric constant of water is virtually independent of frequency up to about 1 GHz.

For most dry soil constituents K is in the range 1 to 4, and dry soil with a pore space of about 50% usually has K approximately 2.6. Water has a much higher dielectric constant of around 78 to 81 for temperatures between 25° C. and 15° C. respectively. K for a soil/water mix is dominated by the large contribution from water. A capacitor embedded in soil will therefore be highly sensitive to the presence of moisture, its capacitance depending on the volumetric water content of the soil sampled by the electric field it produces. In addition to a relatively high dielectric constant most materials containing water will also show appreciable conductivity and this in the past has also been the subject of attempts at moisture detection. Conductivity however, is highly influenced by the presence of dissolved salts, the degree of dissociation of the water molecules and by temperature, K being rather less sensitive. Further, each of these factors is likely to be non-uniform throughout a given volume of soil so isolated measurements remain unsatisfactory.

A sophisticated and expensive instrument currently available uses Time Domain Reflectometry for measurement of dielectric constant. This device times the propagation of a pulse on a transmission line consisting of two parallel rods of a known length, typically 100 cm, and separated by some distance, typically 5 cm. A pulse input at one end of the line is reflected at the other, open end embedded in the material, and the two way trip is timed. Its performance is limited by the length of the transmission line used, which is rigid and on which distortion of the pulse spreads reception time creating an uncertainty of at least 5%.

Dielectric constant measuring apparatus disclosed in U.S. Pat. No. 3,965,416 uses a shorted transmission line as a delay means in determining the frequency of an oscillator. A driver pulses the line and is triggered by the inverted reflection, resulting in an oscillation at a frequency representing the dielectric constant of the material surrounding the line. The device has apparently never been commercially implemented.

SUMMARY OF THE INVENTION

It is an object of the present invention to provide a moisture monitor which allows continuous measurement of moisture content averaged over an extended volume of material, or at least to provide the public with a useful choice.

Accordingly, the invention provides an oscillator comprising an amplifier, a transmission line and frequency output means. The line forms part of a feedback loop of the amplifier and an electrical signal propagating around the loop will be inverted. An electrical oscillation is thereby sustained at a frequency depending on the propagation delay of the line. The line is connected for one-way propagation of the signal around the loop. The output means transmits a measure of the frequency for monitoring of the dielectric constant of the material in which the line is embedded. An increase/decrease in the material moisture content is detected through the corresponding increase/decrease in line delay and consequent decrease/increase in the frequency of the oscillator. Preferably the transmission line is a twin lead cable which may be balanced or unbalanced with respect to ground.

BRIEF DESCRIPTION OF THE DRAWINGS

The preferred form of the invention will be described with reference to the accompanying drawings in which.

DESCRIPTION OF THE PREFERRED EMBODIMENTS

Figure 1:
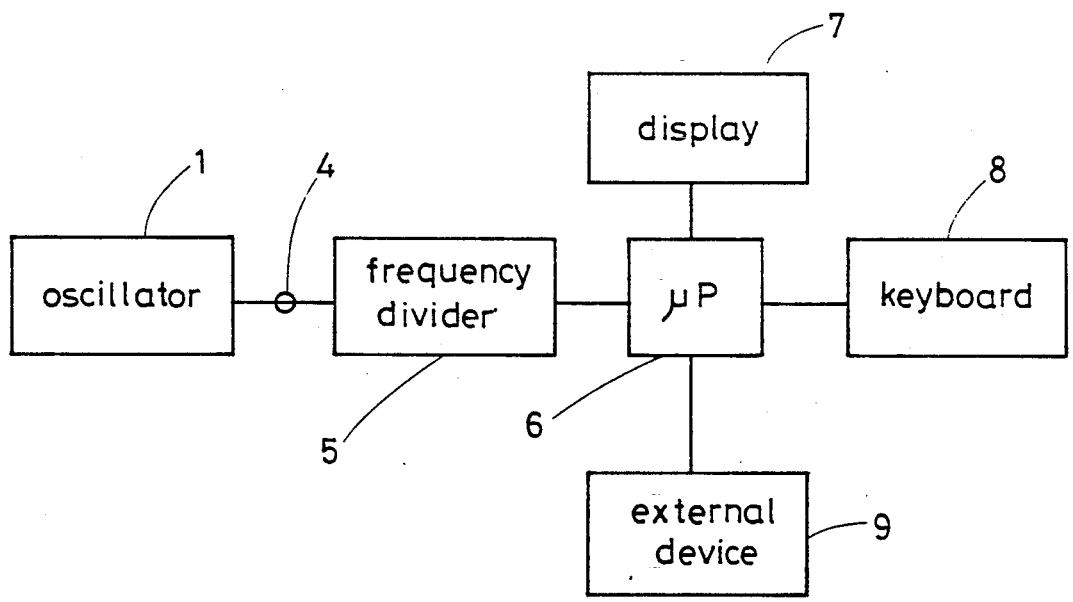
FIG. 1 is a block diagram showing a system incorporating a moisture monitor according to the present invention.

The general scheme for a moisture monitor according to the present invention is shown in FIG. 1. The frequency of an oscillator 1 is determined largely by a transmission line 2, at least partly embedded in soil or some other medium 3. The transmission line is generally a twin lead cable up to perhaps 100 m in length sensitive to the dielectric constant of the medium. An output signal from the oscillator 1 passes from port 4 to a frequency divider 5 and microprocessor 6, which determine from the oscillator frequency a measure of the average dielectric constant of the medium over the length of the line. The oscillator frequencies are typically 1-10 MHz at wavelengths the order of 100-10 m. The display 7 provides a visual indication of the dielectric constant of the medium, for instance by way of an LED display or a graphical or numerical printout. A keyboard 8 allows programming of the microprocessor, which may be connected for control of external devices 9 such as an irrigation system.

The influence of losses due to soil conductivity may be reduced by insulating the line, although the volume of soil sampled and therefore the influence of soil moisture via capacitance is also reduced. Any electrical insulation employed should make only a small contribution to K, comparable to that of the soil, and must be sufficiently constant in time, unaffected by harsh physical or chemical conditions such as freezing or corrosion.

Figure 2:
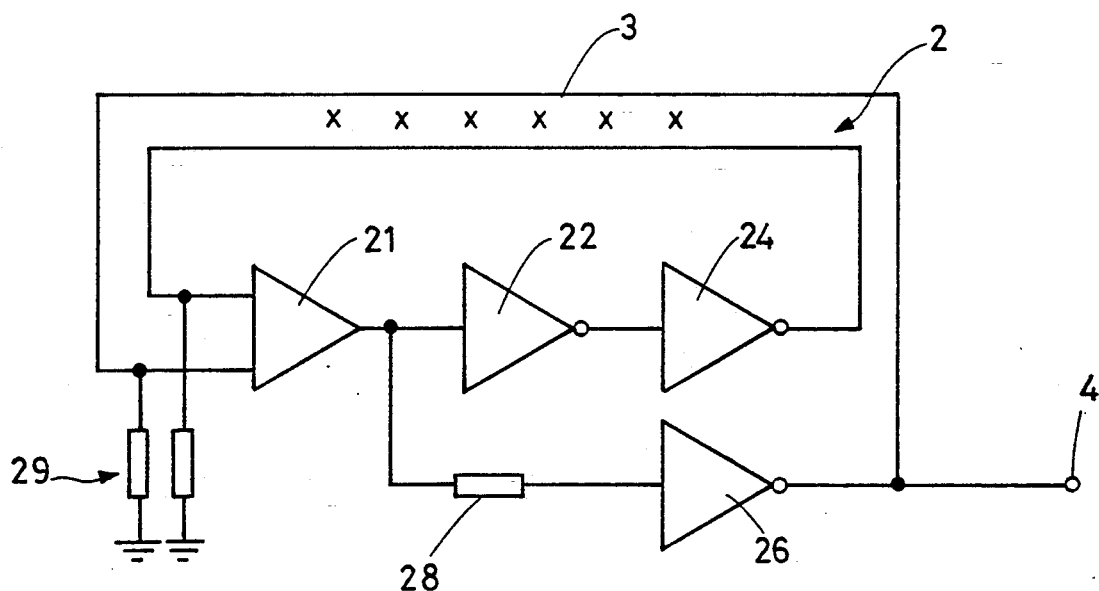
FIG. 2 shows a first embodiment of the oscillator of FIG. 1.
Figure 3:
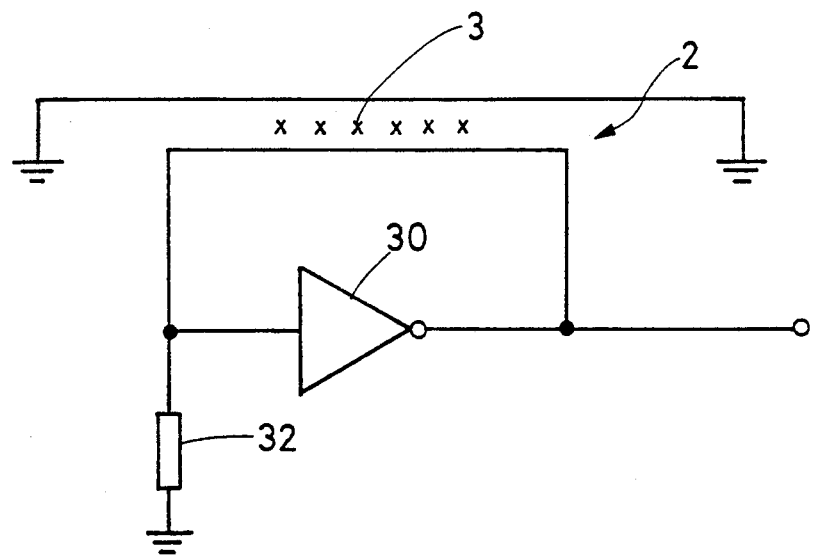
FIG. 3 shows a second embodiment of the oscillator of FIG. 1.
Figure 4:
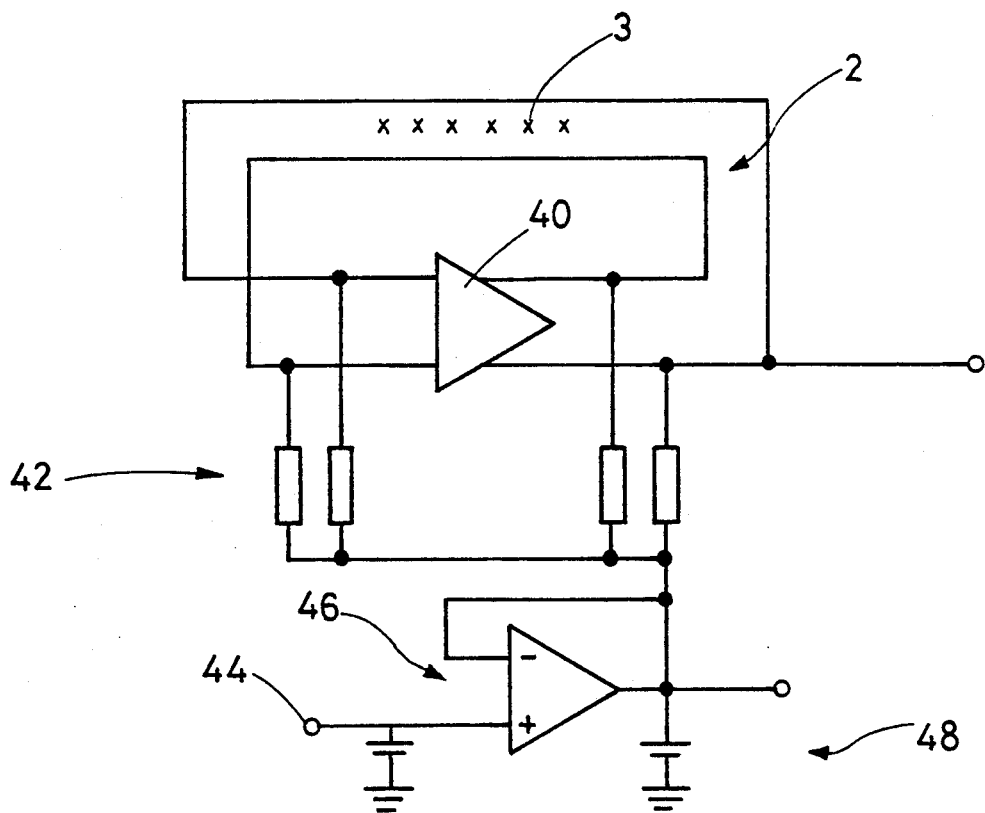
FIG. 4 shows a third embodiment of the oscillator of FIG. 1, FIG. 5 sketches the variation in monitor output during calibration for control of soil moisture content.

FIGS. 2, 3 and 4 show preferred embodiments of an oscillator 1 according to the present invention. The transmission line 2 is connected as a feedback loop of amplifiers 20, 30 and 40 respectively. The amplification and arrangement of each circuit are such that a voltage transition when present will propagate repeatedly around the loop with a nett inversion of once per repeat.

In each of the three embodiments, provided the loop voltage gain of the system is greater than unity, any initial voltage perturbation in the loop will be amplified into a square wave oscillation at a level determined by the maximum output voltage of the amplifier and subject to the amplifier slew rate. The frequency f of the square wave is determined by the propagation delays of the amplifier and transmission line according to $$f = \frac{1}{2(t_a + t_b)}$$

where $t_a$ and $t_b$ are the propagation delays of the amplifier and line respectively. Ideally $t_b$ is much greater than $t_a$ so that variations of $t_a$ with amplifier temperature and supply voltage become relatively insignificant. The oscillator frequency output is consequently largely dependent on the propagation delay of the line which is in turn largely dependent on the line length and average dielectric constant of the surrounding medium.

If the amplifier delay is appreciable relative to that of the line however, a comparison oscillator omitting the line but using other amplifiers of the same integrated circuit package will normally also be connected for output to the microprocessor 6. The signals of each of the two oscillators are then compared by the microprocessor to eliminate the influence of amplifier delays on the monitor output.

Referring to FIG. 2, the amplifier 20 includes a high speed comparator 21 such as provided on Signetics chip SE521. Also included are inverters 22, 24 and 26 such as provided on Phillips chip 74AC11004, to provide a complementary output from the comparator. Nett inversion of a signal propagating on the line 2 is caused by the additional inverter placed in one of the line leads. The balanced line gives good immunity to noise caused by stray capacitance effects between the monitor equipment and ground. Output of the comparator 21 is switched near zero crossings of the input ensuring that inversion of the propagating voltage transition is minimally effected by its shape. Resistor 28 in conjunction with the input capacitance of invertor 26 equalises the delay in each output of the second comparator. Resistors 29 are chosen to approximately match the amplifier 20 to the line, suppressing reflection, although exact matching is impossible as the line characteristics may vary appreciably with the properties of the surrounding material.

Referring to FIG. 3, the amplifier 30 is a high speed inverter such as a 74HCO4 logic gate. The line is unbalanced, the ends of the line which are not connected to the amplifier being connected to a common ground. Impedance 32 approximately matches the amplifier to the line. Although more susceptible to noise, an unbalanced system such as shown in FIG. 3 is simpler to implement than the systems of FIGS. 2 or 4, and has been found satisfactory in measurements of soil moisture content.

Referring to FIG. 4, the amplifier 40 is a balanced high speed line receiver/driver such as provided on Motorola chip MC10114. Nett inversion of a signal propagating on the line 2 is provided by crossing of the line leads between the output and input of the amplifier. The amplifier is biased by resistors 42, which are chosen to approximately match the amplifier to the line. The resistors are connected to the amplifier bias supply at 44 by means of a voltage follower 46, connected as a buffer. Capacitors 48 serve to ensure a smooth supply with low source impedance at the oscillation frequency.

Output of the present monitor may be calibrated by any of several methods. If the delay of the line in a known state of the surrounding material and the delay of the remaining oscillator circuitry are measured or calculated at a particular frequency, a subsequent variation in frequency may be used to calculate the variation in moisture, assuming other contributions to the dielectric remain fixed. For example, the monitor output reading may be compared with determinations of moisture content by point measurements taken along the length of the line, using standard techniques as earlier described. In practice it may be more convenient to calibrate the monitor empirically as described next with reference to agricultural soil moisture measurements.

Figure 5:
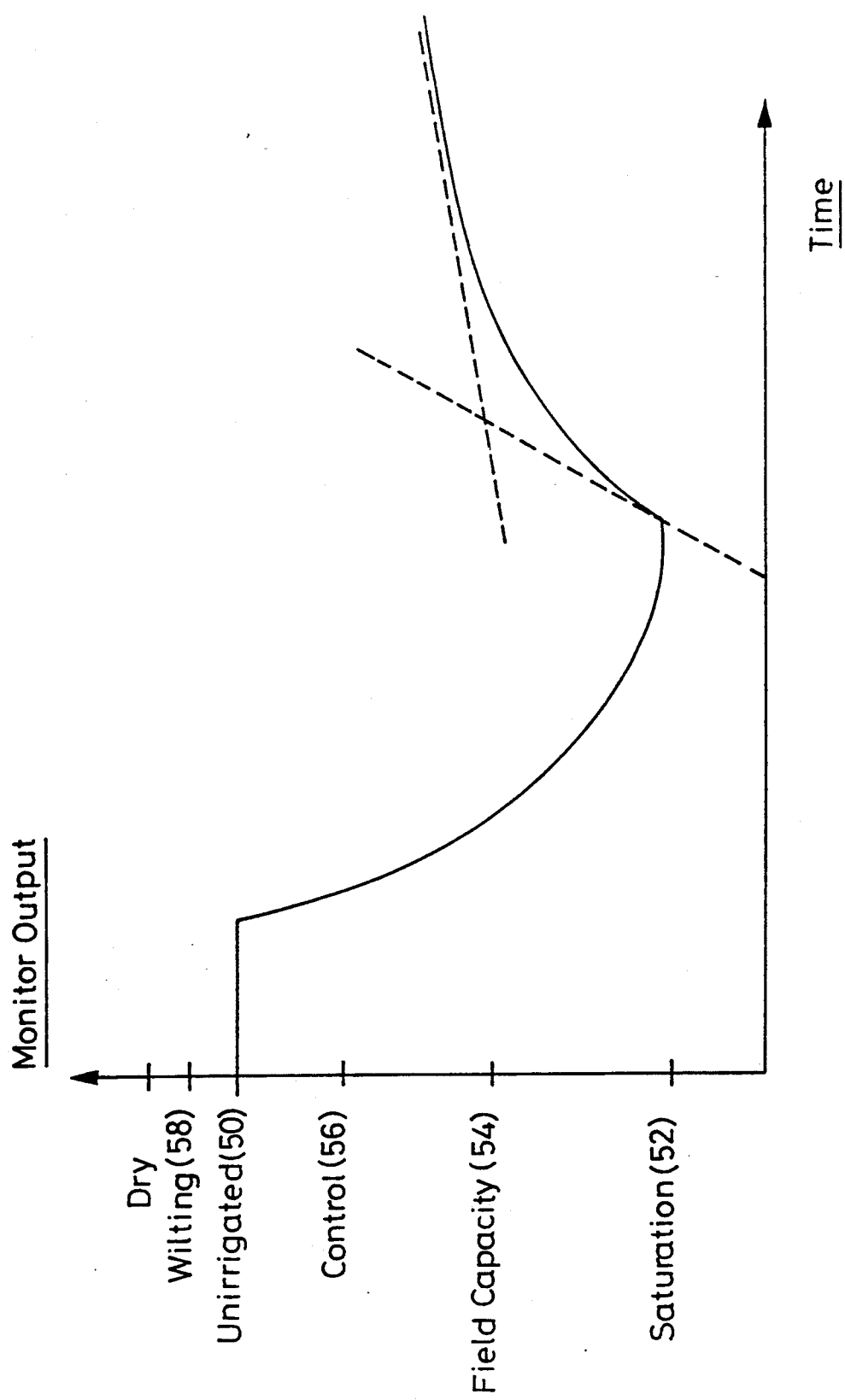

Referring to the sketch of FIG. 5, the monitor output reading 50 of unirrigated soil is recorded. The soil is then irrigated evenly until there is no further decrease in reading.

At this stage the soil is at saturation 52 and its pore space is completely filled with water. Irrigation is then halted, and assuming no rain fall, the oscillator frequency and monitor output will increase as the pore space drains under gravity. The drainage rate is substantially reduced as the soil water content approaches the field capacity 54, the rate becoming dependent more on plant root extraction and evaporation from the soil surface. The rate of output increase does not change abruptly, and to estimate the field capacity, the straight line portion of the drainage curve obtained may be extrapolated to their intersection. Having established a monitor reading for soil saturation and field capacity, a typical moisture control reading 56 would be greater than that of field capacity by about the difference between saturation and field capacity. The control reading will of course depend on the nature of the crop to be irrigated.

The output of a series of monitors such as described herein, may be incorporated within an overall monitoring/controlling system perhaps including daisy-chained cables, block irrigation scheduling, and a user-friendly interface for input and output of data. The latter may comprise graphical output of moisture levels, temperature, conductivity, water usage or other information relevant to the desired application.

It is evident that numerous variations in the oscillator and output circuitry are possible without departing from the scope of the invention described and claimed. It is also evident that a monitor according to the present invention may be applied in a broad range of circumstances where monitoring of the dielectric constant of a large volume of material is required.

What is claimed is:

1. Apparatus for monitoring the dielectric constant of a material comprising:
    an amplifier having input and output ports,
    a transmission line connected at one end to the amplifier input and at the other end to the amplifier output forming a feedback loop, and
    output means connected to the loop; wherein
    the transmission line is embedded at least partly in the material when monitoring takes place,
    an electrical signal propagates one-way along the transmission line and through the amplifier in passing around the loop,
    the signal is inverted on each passage around the loop to sustain an electrical oscillation at a frequency determined in part by the propagation delay of the transmission line, and
    the oscillation frequency is used by the output means to provide a measure of the dielectric constant of the material.

2. Apparatus according to claim 1 wherein the transmission line comprises a twin lead cable.

3. Apparatus according to claim 1 wherein the amplifier comprises an inverter connected to one lead of the transmission line, and a comparator.

4. Apparatus according to claim 1 wherein the electrical signal is inverted by the amplifier.

5. Apparatus according to claim 2 wherein the electrical signal is inverted by crossing the leads of the cable between connection of the transmission line to the amplifier input and the amplifier output.

6. Apparatus according to claim 1 wherein the transmission line is unbalanced with respect to ground.

7. Apparatus according to claim 1 further comprising:
    a comparison amplifier having input and output ports,
    a relatively-short length transmission line connected at one end to the comparison amplifier input and at the other end to the comparison amplifier output comprising a second feedback loop, and
    second output means connected to the second feedback loop;
    wherein an electrical signal propagating around the second feedback loop will be inverted and a comparison electrical oscillation will be sustained at a frequency determined largely by the propagation delay of the comparison amplifier, and
    the comparison oscillation frequency is used by the second output means for correction of the measure of the dielectric constant of the material.

8. A method of monitoring the dielectric constant of a material comprising:
    embedding a transmission line in the material as part of an amplifier feedback loop,
    propagating an electrical signal one-way along the transmission line and through the amplifier,
    inverting the signal on each passage around the loop to create an electrical oscillation at a frequency determined in part by the propagation delay of the transmission line, and
    using the frequency to provide a measure of the dielectric constant of the material.

9. A method according to claim 8 further comprising correcting the measure of the dielectric constant by comparison of the frequency with a second frequency output from a second amplifier and feedback loop having a relatively-short transmission line not embedded in the material but otherwise substantially identical to the first amplifier and feedback loop.

* * * * *